(12) United States Patent
Shiokawa (10) Patent No.: US 7,336,992 B2
(45) Date of Patent: Feb. 26, 2008

(54) BODY COMPOSITION MEASURING DEVICE

(75) Inventor: Takashi Shiokawa, Tokyo (JP)

(73) Assignee: Tanita Corporation, Tokyo (JP)

( * ) Notice: Subject to any disclaimer, the term of this patent is extended or adjusted under 35 U.S.C. 154(b) by 46 days.

(21) Appl. No.: 11/067,947

(22) Filed: Mar. 1, 2005

(65) Prior Publication Data
US 2005/0192511 A1    Sep. 1, 2005

(30) Foreign Application Priority Data
Mar. 1, 2004 (JP) ............................. 2004-056352
Dec. 10, 2004 (JP) ............................. 2004-358438

(51) Int. Cl.
*A61B 5/05* (2006.01)
(52) U.S. Cl. ....................................................... 600/547
(58) Field of Classification Search ................ 600/547, 600/546
See application file for complete search history.

(56) References Cited

U.S. PATENT DOCUMENTS

| 4,831,324 A | 5/1989 | Askura et al. |
| 5,579,782 A | 12/1996 | Masuo et al. |
| 6,532,384 B1 * | 3/2003 | Fukuda ........................ 600/547 |

FOREIGN PATENT DOCUMENTS

| EP | 1 080 686 A1 | 3/2001 |
| JP | 09-154829 | 6/1997 |
| JP | 2000-023935 | 1/2000 |
| JP | 2004-255120 | 9/2004 |

OTHER PUBLICATIONS

Thomas et al., "Bioimpedance Spectrometry in the Determination of Body Water Compartments: Accuracy and Clinical Significance", *Appl. Radiat. Isot.* vol. 49, No. 5/6, pp. 447-455, 1998.

Nawarycz et al., "Triple - Frequency Electroimpedance Method for Evaluation of Body Water Compartments", Medical & Biological Engineering & Computing vol. 34, 1996, pp. 181-182.

* cited by examiner

*Primary Examiner*—Max F. Hindenburg
*Assistant Examiner*—Jonathan Foreman
(74) *Attorney, Agent, or Firm*—McDermott Will & Emery LLP (57) ABSTRACT

An object of the present invention is to provide a body composition measuring device used in arithmetically deriving an index indicative of body composition in accordance with the bioelectric impedance measuring method, in which a highly accurate calculation result can be obtained with the reduced effect from the fluctuation in a day while using a simple measuring method. Provided is a body composition measuring device in which the bioelectric impedance value is measured at each different frequency by applying the current at a plurality of different frequencies, for example, at a first frequency and a second frequency, to the living body, while concurrently correcting the measured bioelectric impedance value at the first frequency or at the second frequency by using the difference in the bioelectric impedance values between the first and the second frequencies to calculate the index indicative of the body composition based on the corrected bioelectric impedance value, or while concurrently calculating the index indicative of the body composition based on either one of the measured bioelectric impedance values at the first frequency or at the second frequency and then correcting the calculated index indicative of the body composition by using the difference between the bioelectric impedance values at the first and the second frequencies.

1 Claim, 10 Drawing Sheets

BODY COMPOSITION MEASURING DEVICE

FIELD OF THE INVENTION

The present invention relates to a device for measuring bioelectric impedance and for arithmetically deriving a variety of body indices based on a measured value of the bioelectric impedance.

DESCRIPTION OF THE PRIOR ART

It has been made possible to measure a bioelectric impedance and to arithmetically derive indices indicative of body composition, including a body fat percentage, a muscle mass and an amount of total body water, based on a measurement of the bioelectric impedance as well as a subject's height and body weight, and such a device enabling the above performance has already been available broadly in the market. However, it has been recognized in association with the bioelectric impedance value that a fluctuation called as fluctuation in a day is observed in a day and this fluctuation emerges as an error in deriving the body index such as the body fat percentage. There has been known a technology for correcting the bioelectric impedance value in which a day is divided into a plurality of time zones and the measured impedance value is corrected as a function of each time zone to reduce this error resultant from the fluctuation in a day (see, for example, Patent Document 1).

Although the bioelectric impedance measurement for arithmetically determining the body index is typically performed by using a current of single frequency around a characteristic (critical) frequency, there is also a known technology using a current of multi-frequency for measuring the bioelectric impedance to thereby provide a more accurate calculation of the body fat percentage (see, for example, Patent Document 2).

[Patent Document 1]
Japanese Patent Laid-open Publication No. 2000-23935

[Patent Document 2]
Japanese Patent Laid-open Publication No. Hei 9-154829

SUMMERY OF THE INVENTION

It could occasionally happen in arithmetically deriving a body fat percentage by using the bioelectric impedance measuring method that a derived body fat percentage is actually varied in such a short time period that is believed to be typically free from any fluctuation in body fat percentage. The bioelectric impedance measuring method can measure electric characteristics of electrolyte contained in a living body. In this regard, distribution of water in vivo varies in various ways during a day resultant from increase or decrease in an amount of the body water due to an exercise and/or a meal and/or a stagnant body water due to sleeping and/or being inactive. This represents a phenomenon referred to as the fluctuation in a day, and the change in distribution of the body water does effect as an error factor to the measurement results of the bioelectric impedance and/or the body fat percentage derived therefrom. In the device disclosed in the Japanese Patent Laid-open Publication No. 2000-232935, the fluctuation in a day is taken into account to correct a measured impedance value. However, since the device uses a set of measured data effective at a present time and a set of measured data effective for the other time to make a correction on the resultant bioelectric impedance, it needs the data measured at separate times with a long interval therebetween, such as the data to be measured in the morning and the data to be measured in the evening. Owing to this, the correction could not be applied immediately at the time of an initial measurement but a long time period should be necessary to obtain the effect from the correction.

Further, according to the calculation of the body fat percentage in a multi-frequency impedance measurement disclosed in the Japanese Patent Laid-open Publication No. Hei 9-154829, an expected impedance at the infinite frequency is derived from a locus of the actual bioelectric impedance, and based on the derived value as well as items characterizing a body for a subject, including height, body weight, sex and age, the body fat percentage of the subject is estimated. However, even if the body fat percentage would be calculated by using such multi-frequency impedance measurement, the change in the amount of body water called as fluctuation in a day could emerge as the change in the body fat percentage.

In the above situation, the applicant of the present invention has disclosed, in the Specification of the Japanese Patent Application No. 2003-052257, one technology relating to the art for measuring body composition from electric characteristics of a living body, in which the bioelectric impedance is divided into a resistance and a reactance through the detection of a phase difference in applied current, and based on a value obtained in the above manner, the body composition of the subject is estimated. According to this technology, the fluctuation in a day can be suppressed by using the reactance as a parameter representing a ratio of intracellular to extracellular fluid in order to correct the bioelectric impedance value.

However, this correction method requires the measurement of the phase difference between the current applied to the living body and the voltage thereof in order to detect the resistance and the reactance. To address this, a phase difference detecting device must be disposed between a current supplying device for supplying a current to the living body and a voltage measuring device for measuring a voltage flowing through the living body.

The above technology further requires, in addition to the phase difference detecting device, an arithmetic operation (program) for computing the resistance and the reactance from the phase difference measured by the phase difference detecting device, and accordingly such equipment including the above designated elements could ultimately need more complicated configuration/means as compared to the conventional equipment for performing exclusively the bioelectric impedance measurement.

The present invention has been made in the light of the problems described above and an object thereof is to provide a body composition measuring device used in arithmetically deriving an index indicative of body composition, such as a body fat percentage, in accordance with the bioelectric impedance measuring method, in which a highly accurate calculation result can be obtained with the reduced effect from the fluctuation in a day while using a simple measuring method, and thus an accurate body index can be derived at all times.

A body composition measuring device of the present invention comprises: a current applying unit which applies a current at a first frequency and a current at a second frequency to a living body; a voltage measuring unit which measures a voltage induced in the living body from the application of the current; a bioelectric impedance calculation unit which calculates a bioelectric impedance value for each frequency from the applied current and the measured voltage; and a body composition calculation unit which calculates an index indicative of the body composition based on the calculated bioelectric impedance value, said device characterized in that:

said bioelectric impedance calculation unit corrects the bioelectric impedance value at the first frequency or at the second frequency by using a difference between the bioelectric impedance value at the first frequency and the bioelectric impedance value at the second frequency; and said body composition calculation unit calculates the index indicative of the body composition based on the corrected bioelectric impedance value.

An alternative body composition measuring device of the present invention comprises: a current applying unit which applies a current at a first frequency and a current at a second frequency to a living body; a voltage measuring unit which measures a voltage induced in the living body from the application of the current; a bioelectric impedance calculation unit which calculates a bioelectric impedance value for each frequency from the applied current and the measured voltage; and a body composition calculation unit which calculates an index indicative of the body composition based on the calculated bioelectric impedance value, said device characterized in that;

said body composition calculation unit corrects the index indicative of the body composition, that has been calculated based on either one of the bioelectric impedance value at the first frequency or the bioelectric impedance value at the second frequency, by using a difference between the bioelectric impedance value at the first frequency and the bioelectric impedance value at the second frequency. Especially in this case, said body composition calculation unit corrects the index indicative of the body composition in accordance with the following equation for correction:

$$P'=P+[a \times P \times \{Z(F_1)-Z(F_2)\}/Z(F_2)+b],$$

where

P': the corrected index indicative of the body composition,

P: the calculated index indicative of the body composition before correction, $Z(F_1)$: the bioelectric impedance at the first frequency, $Z(F_2)$: the bioelectric impedance at the second frequency and a, b: constants.

Further a body composition measuring device of the present invention is characterized in that said first frequency is defined as a frequency close to 0 Hz, and said second frequency is defined as a frequency close to a characteristic frequency.

The body composition measuring device according to the present invention is operable to provide the measurement of the bioelectric impedance value at each different frequency by applying the current at many different frequencies, for example, at the first frequency and the second frequency, to the living body, while concurrently correcting the measured bioelectric impedance value at the first frequency or at the second frequency by using the difference in the bioelectric impedance value between the first and the second frequencies to calculate the index indicative of the body composition based on the corrected bioelectric impedance value, or while concurrently calculating the index indicative of the body composition based on either one of the measured bioelectric impedance values at the first frequency or at the second frequency and then correcting the calculated index indicative of the body composition by using the difference between the bioelectric impedance values at the first and the second frequencies, thereby allowing for the calculation of the body composition with the reduced effect from the fluctuation in body water content distribution which is called as the fluctuation in a day.

Further advantageously, the correcting operation performed by the body composition measuring device of the present invention simply uses the difference between the bioelectric impedance values measured at two difference frequencies as the parameter, allowing for its simple configuration, shorter time required for the measurement and thus its implementation without any particularly complicated operating processes.

DESCRIPTION OF THE PREFERRED EMBODIMENTS

Providing a description on an embodiment of the present invention, firstly, the principle of bioelectric impedance measurement will be described.

Figure 1:
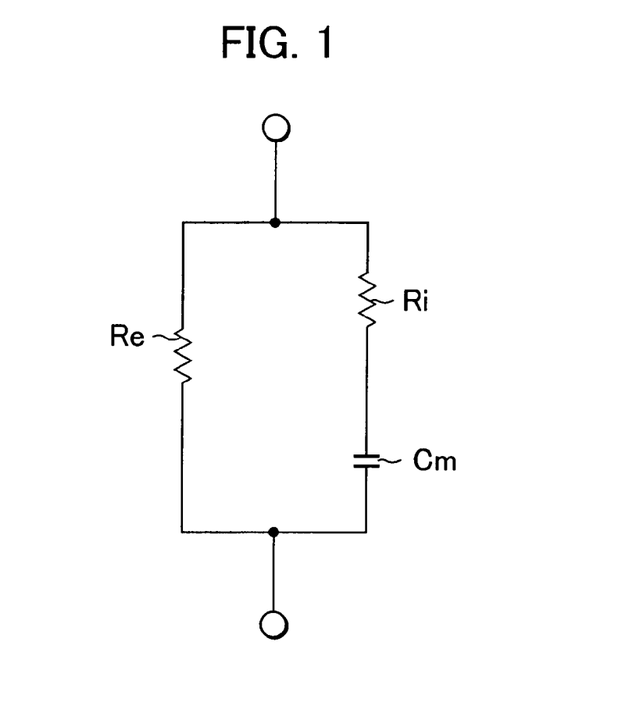
FIG. 1 is a diagram showing an electrical equivalent circuit of a cell in tissue.

A bioelectric impedance value is typically described in such an equivalent circuit of lumped constants as illustrated in FIG. 1 consisting of an extracellular fluid resistance, Re, an intracellular fluid resistance, Ri, and a cell membrane capacitance, Cm. A current flowing through a living body during the measurement of the bioelectric impedance would flow primarily in segments defined by the extracellular fluid and the intracellular fluid, which are characterized by containing electrolyte composition and by lower resistivity. However, the intracellular fluid segment is surrounded by an extremely thin cell membrane, which can be considered as an insulating membrane. This insulating membrane is represented as a capacitor (Cm) in the equivalent circuit of FIG. 1, through which no direct current can flow and whose impedance varies inversely proportional to a frequency. Owing to this, the value of the current flowing through the intracellular fluid segment depends on the frequency of the flowing current.

Figure 2:
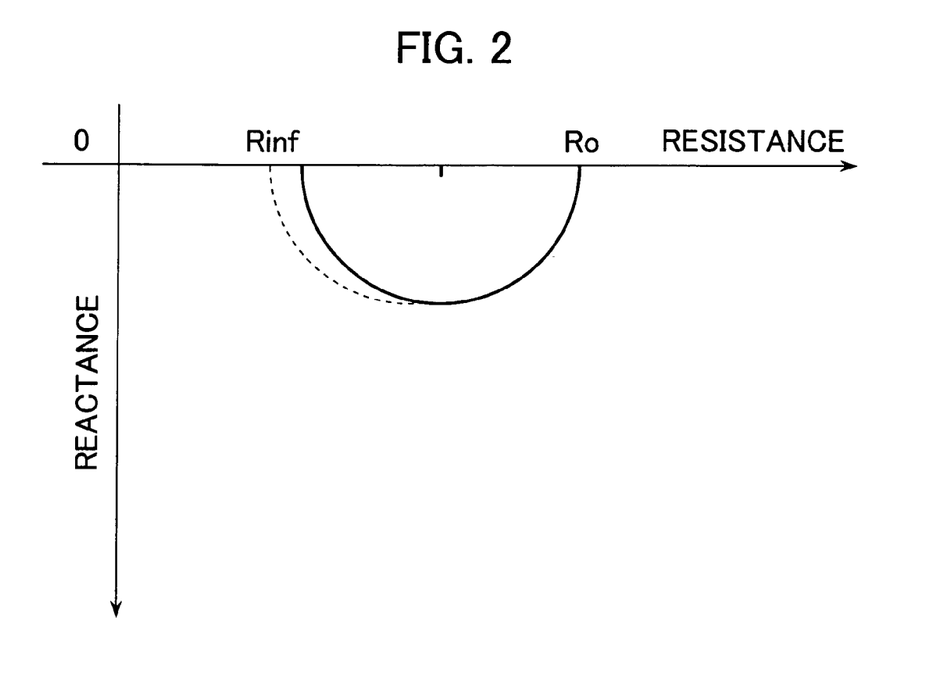
FIG. 2 is a diagram representing a bioelectric impedance vector locus for a human body.

On the other hand, the extracellular fluid segment exhibits a constant resistance value independently from the frequency of the flowing current, as indicated in the equivalent circuit of FIG. 1 as the extracellular fluid resistance (Re). Actually, each individual cell constituting a living body maybe represented by an individually designated circuit with different constants, depending on its distinctive shape and property. It is believed based on this fact that, in a living body embodying a collective entity of individual cells, the impedance vector locus would not follow a semi-circle as is the case for measuring the equivalent circuit of lumped constants but would draw an arc in accordance with the Cole-Cole's arc law. Accordingly, the bioelectric impedance would generally draw such an arc locus as shown in FIG. 2. In FIG. 2, a horizontal axis represents a resistance of impedance and a vertical axis represents a reactance of the impedance. The reactance of the bioelectric impedance is capacitive and thus represented by a negative value, whose vector locus appears below the real axis as shown in FIG. 2.

Assuming that the vector locus to be determined would follow an arc, respective bioelectric impedance values, Z1, Z2, . . . , Zn, measured at the frequencies of Fi (i=1 to n) should be as illustrated in FIG. 2. When a horizontal axis representing the real axis on the impedance vector plane in FIG. 2 is taken as the X axis and a vertical axis representing the imaginary axis on that plane is taken as the Y axis, intersection points of the vector locus with the X axis are denoted as $R_o$ and $R_{inf}$ (or $R_\infty$). With this conditioned, the body fat percentage can be now calculated based on the determined impedance vector locus and its associated parameters, including $R_o$ and $R_{inf}$, as well as respective values indicative of sex, height, weight and age, which have been input as personal parameters, in accordance with a known calculating method.

On the other hand, the bioelectric impedance measurement using a single frequency, which is currently practiced generally as the method for measuring the body water content or the body composition, uses an alternating current at a frequency close to 50 kHz, which represents the frequency close to the characteristic frequency, Fc ($1/2\pi\tau$), according to the Cole-Cole's arc law. Over this frequency zone, although the measuring current can flow throughout the extracellular fluid segment, it is subject to the effect from the impedance of the cell membrane and so only the current as small as some part of the total current that would flow at the infinite frequency can flow into the intracellular fluid segment. However, it is possible to evaluate the body water content and the body composition by taking such electrical characteristics of the living body into account. It is to be noted that since the intracellular fluid segment has a smaller effect on the bioelectric impedance than the extracellular fluid segment, various problems has caused in the actual practice. Some of them will now be described by way of example.

The extracellular fluid is generally composed of blood, lymph fluid and intercellular fluid and comparatively tends to be moved due to the effect from gravity and so on, while on the contrary the intracellular fluid can move through the cell membrane and so needs a relatively long time period to move. This implies the possibility that only the distribution of the extracellular fluid may change easily yet in a short time depending on a measuring site and a measuring pose during the measurement of the bioelectric impedance. From the reason that the effect from the extracellular fluid segment to the bioelectric impedance is greater than that from the intracellular fluid segment, as described above, such a change in the distribution of the extracellular fluid may emerge to be a major fluctuation in the measured value of the bioelectric impedance, resulting in an error in the estimation of the body water content or the body composition.

There is another possible case leading to the error in the estimation of the body water content or the body composition for a subject having a ratio of the extracellular fluid to the intracellular fluid significantly different from those of the standard persons. For example, such an athlete having a distinguishably large muscle mass as compared to the standard people may have a larger intracellular fluid segment than that of the standard people corresponding to the extent of the muscle development and is accordingly considered to have a greater ratio of the intracellular fluid in the body water content as compared to the standard people, but from the reason that the intracellular fluid segment tends to be underestimated in the bioelectric impedance measurement at a frequency close to the characteristic frequency, as described above, disadvantageously the intracellular fluid and thus the total body water content volume would be underestimated.

This kind of problem should be possibly arisen not only in the measurement at a frequency near to the characteristic frequency but also in the estimation of the body water content and/or the body composition based on the bioelectric impedance measurement at the finite frequency where the extracellular fluid segment and the intracellular fluid segment would not be evaluated evenly.

As discussed previously, the bioelectric impedance measurement with the multi-frequency performs n-time of measurements of the bioelectric impedance value in total for the differently specified n frequencies, Fi (i=1 to n, n is a predetermined set value), respectively. Although this is intended to improve the measurement accuracy of the body water content, disadvantageously the measuring time would be longer to perform a number of bioelectric impedance measurements and also any fluctuation in extracellular fluid volume could be calculated as the fluctuation in body fat when the body fat is derived from the body water content volume, in which method, if applied, the resultant measurement indicates that the body fat has been apparently changed, which would not change by any chance in a short time period.

Figure 3:
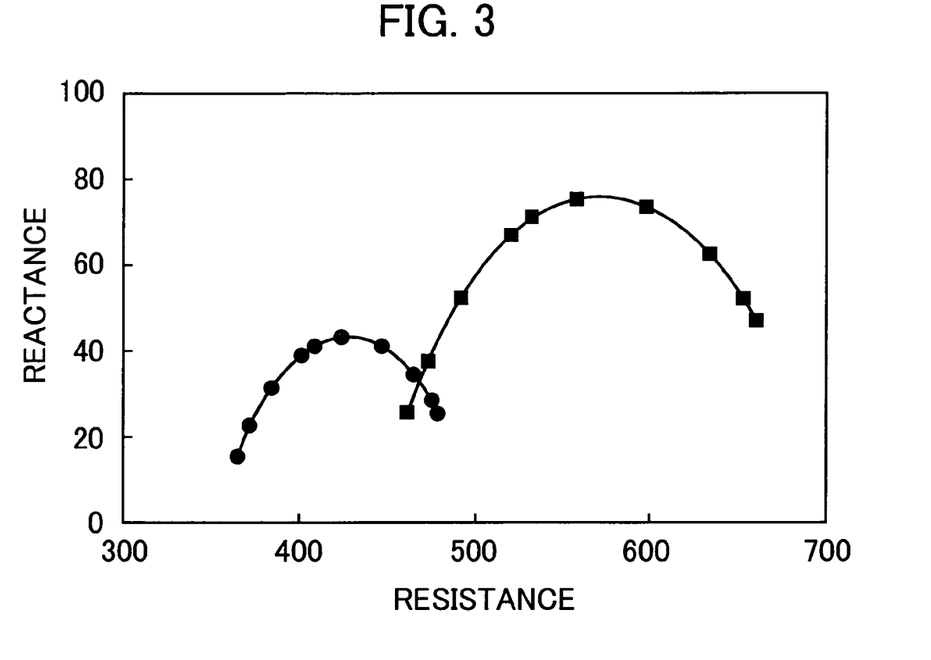
FIG. 3 is a plot showing a fluctuation in the bioelectric impedance vector locus for a human body.

FIG. 3 schematically shows an arc locus of impedance in the multi-frequency bioelectric impedance measurement. The change in the body water content is also reflected in the fluctuation in the vector locus, resulting in such a change as illustrated in FIG. 3, for example. The location and size of the vector locus measured at a certain time changes in association with the fluctuation in the body water content volume. Such a change has affected to the calculation of the body composition, such as the body fat. Inevitably, the bioelectric impedance measurement, even if using the multi-frequency, has been still suffered from the problem that the effect from the fluctuation in the body water content is reflected in the measurement result. It is to be noted that since the reactance of the bioelectric impedance is capacitive and accordingly represented by a negative value, FIG. 2 shows the vector locus below the real axis, but FIG. 3 shows the vector locus in the upper region with respect to the real axis for convenience in description under the assumption that the negative values are represented in the upper side of the real axis.

In this regards, in the Specification of the Japanese Patent Application No. 2003-052257, which has been applied by the applicant of the present invention, the resistance and the reactance are detected from a phase difference in the measured bioelectric impedance value and those parameters are used in the correction of the bioelectric impedance, thereby achieving the improvement in measurement accuracy without performing the bioelectric impedance measurement at a number of different frequencies.

However, the detection of the resistance and the reactance requires to measure the phase difference between the current and the voltage applied to a living body, and thus a phase difference detecting device must be provided between a current supply device for supplying the current to the living body and a voltage measuring device for measuring the voltage of the current flowing through the living body.

The above arrangement further needs, in addition to the phase difference detecting device, an arithmetic operation (program) for computing the resistance and the reactance from the phase difference measured by the phase difference detecting device, and such equipment including the above designated elements could ultimately need more complicated configuration/means as compared to the conventional equipment for performing exclusively the bioelectric impedance measurement.

In the light of the above condition, the present invention is intended to provide the measurement accuracy as high as that can be achieved by the art for correcting the bioelectric impedance as disclosed in the above-stated Specification of the Japanese Patent Application No. 2003-052257 yet with much simpler configuration and arithmetic operation without requiring the measurement of the phase difference to be executed in the measurement of the bioelectric impedance.

In the above-mentioned Cole-Cole's arc law, the value of the reactance (Y axis) is maximal for the bioelectric impedance value at the characteristic frequency Fc ($1/2\pi\tau$). This implies that when the arc locus is moved due to the fluctuation in the body water content volume as illustrated in FIG. 3, the extent of the fluctuation in the reactance at the characteristic frequency is greater than the fluctuation in the reactance at a frequency close to 0 Hz (F0) or close to the infinite frequency ($F_\infty$), and thus the effect from the fluctuation in the body water content volume should emerge most distinctively at the characteristic frequency. That is, observation of the fluctuation in the reactance at a frequency close to the characteristic frequency, Fc, allows to easily determine the fluctuation in the body water content volume during the measurement. In other words, selecting the reactance value at a frequency close to the characteristic frequency, Fc, as the measuring parameter provides a greater effect on the correction.

Figure 4:
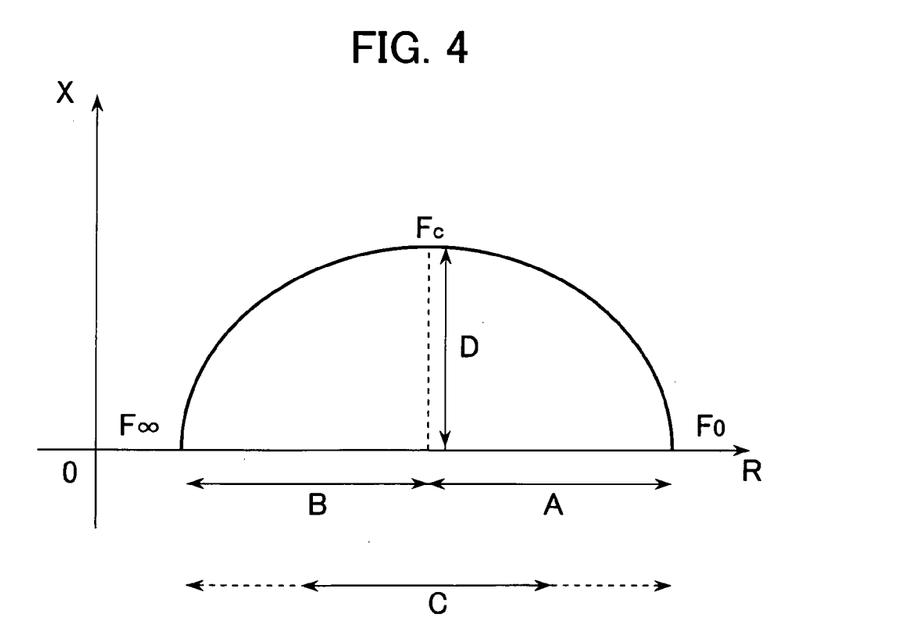
FIG. 4 is a diagram representing a relationship between a resistance value and a reactance value in a bioelectric impedance vector locus for a human body.

Further, assuming that the center of arc in the Cole-Cole's arc resides on the real axis as illustrated in FIG. 4, the difference between the resistance value at the frequency of 0 Hz, R0, and the resistance value at the characteristic frequency Fc, Rc, (i.e., A component in FIG. 4); the difference between the resistance value at the characteristic frequency Fc, Rc, and the resistance value at the infinite frequency, $R_\infty$, (i.e., B component in FIG. 4); and one-half of the difference between the resistance value at the frequency of 0 Hz, R0, and the resistance value at the infinite frequency, $R_\infty$, (i.e., C component in FIG. 4) are respectively equal to the reactance value at the characteristic frequency, Xc, (i.e., D component in FIG. 4), which respectively represent the radius of the Cole-Cole's arc.

In spite of the fact that some degree of offset in the center of the Cole-Cole's arc can be often observed in the actual measurement of the living body and in those cases the above-designated three types of resistance values (A, B and C components in FIG. 4) would not be equal to the reactance value (D component in FIG. 4), yet a very good correlation can be seen between respective resistance values and the reactance value.

Figure 5:
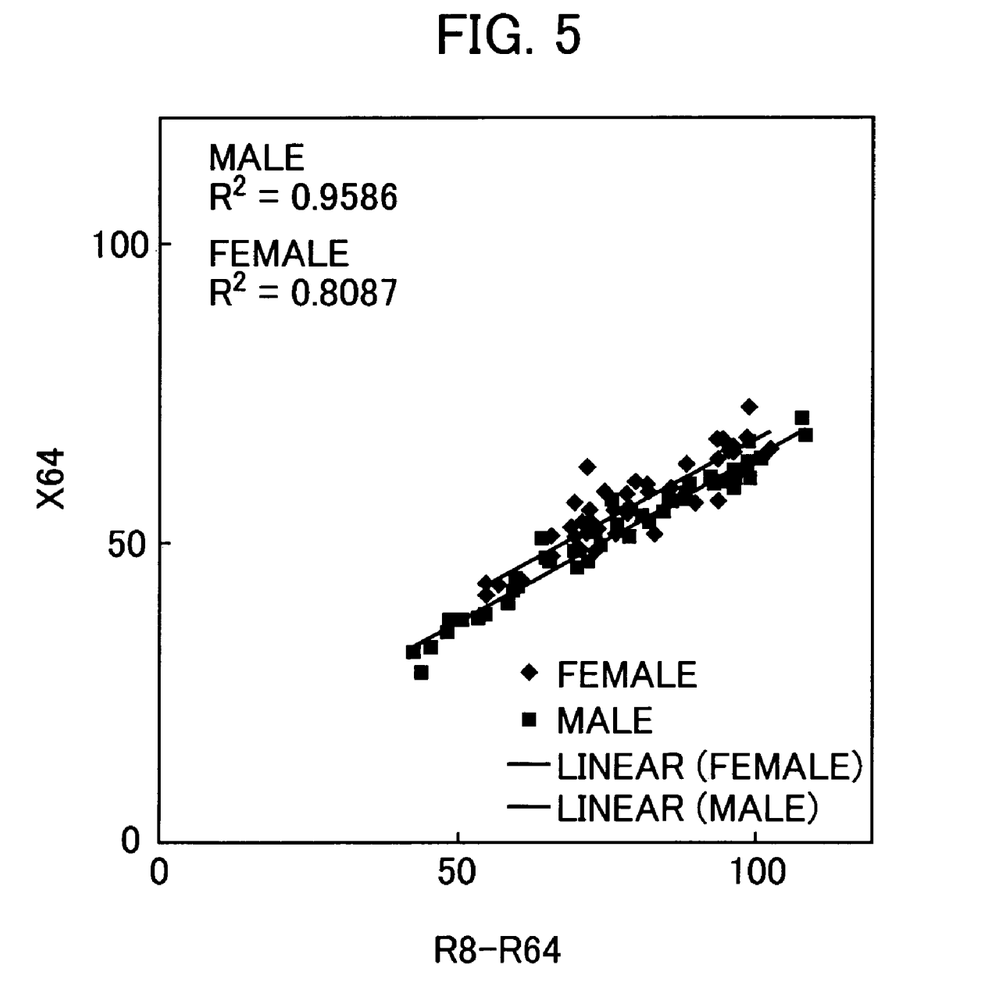
FIG. 5 is a graphical representation indicative of a relationship between a reactance value at a frequency close to a characteristic frequency and a difference between the resistance values at a frequency close to 0 Hz and at a frequency close to a characteristic frequency.

FIG. 5 shows a relationship between the reactance value at 64 kHz (i.e., vertical axis) and the difference between the resistance values at 8 kHz and at 64 kHz (i.e., horizontal axis) in the measurement of the bioelectric impedance conducted for a plurality of subjects at two different frequencies, 8 kHz close to the frequency of 0 Hz and 64 kHz close to the characteristic frequency Fc.

FIG. 5 plots a linear and correlational coefficients separately for male and female subjects, and the high correlation coefficients have been obtained at $R^2=0.958$ for male subjects and $R^2=0.8087$ for female subjects, indicating that significant correlations have been obtained in both sexes.

Figure 6:
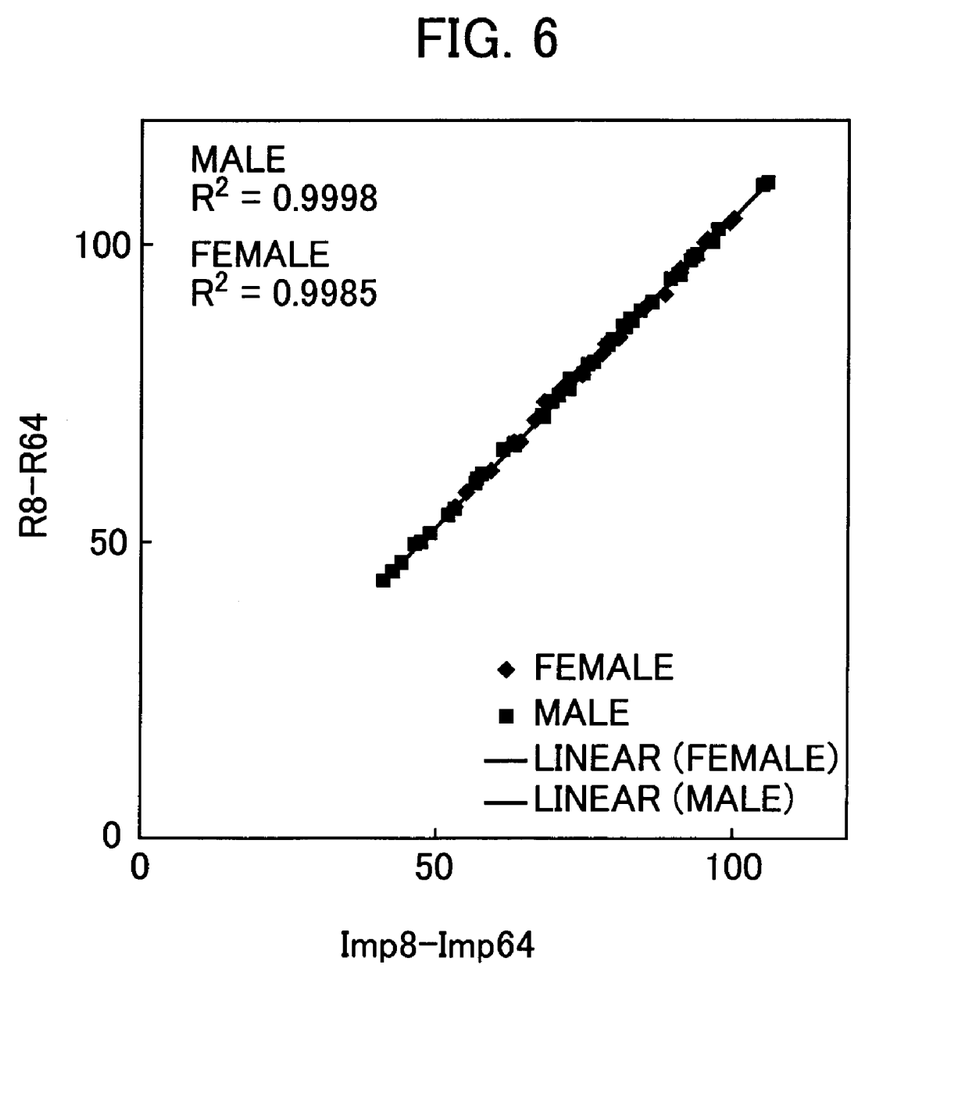
FIG. 6 is a graphical representation indicative of a relationship between a difference in the resistance value and a difference in the impedance value, respective differences in the resistance and in the impedance being defined between the values at a frequency close to 0 Hz and at a frequency close to a characteristic frequency, respectively.

From the reason that the impedance value, Z, and the resistance value, R, are highly approximate to each other in the bioelectric impedance measurement, they are often treated as Z≈R. FIG. 6 shows the relationship between the difference in the resistance value (i.e., vertical axis) and the difference in the impedance value (i.e., horizontal axis), respective differences in the resistance and in the impedance being defined between the values at a frequency of 8 kHz and at a frequency of 64 kHz under the measuring condition specified with respect to FIG. 5.

Quite high correlation coefficients have been obtained, $R^2=0.9998$ for male subjects and $R^2=0.9985$ for female subjects. This implies that instead of the difference between the resistance values at 8 kHz and at 64 kHz, the difference between the impedance values at 8 kHz and at 64 kHz, if used, allows for the correlation with the reactance value at 64 kHz to be obtained.

Figure 7:
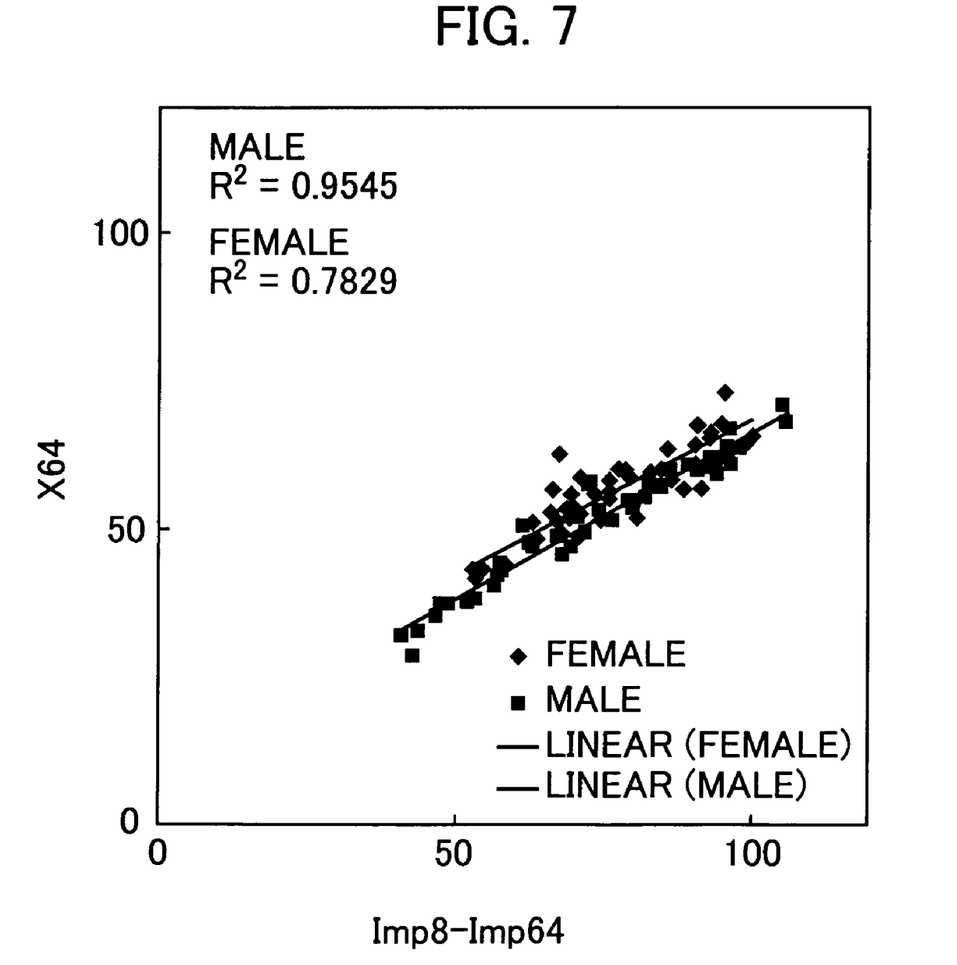
FIG. 7 is a graphical representation indicative of a relationship between a reactance value at a frequency close to a characteristic frequency and a difference between the impedance values at a frequency close to 0 Hz and at a frequency close to a characteristic frequency.

As it is, the observation is now directed to the correlation between the reactance value at 64 kHz and the difference between the impedance values at 8 kHz and at 64 kHz. FIG. 7 shows a relationship between the reactance value at 64 kHz (i.e., vertical axis) and the difference between the impedance values at 8 kHz and at 64 kHz (i.e., horizontal axis) in the measurement of the bioelectric impedance conducted for a plurality of subjects at two different frequencies, 8 kHz close to the frequency of 0 Hz and 64 kHz close to the characteristic frequency Fc.

Again, FIG. 7 shows a linear and correlational coefficients separately for male and female subjects and high correlation coefficients have been obtained, such as $R^2=0.9545$ for male subjects and $R^2=0.7829$ for female subjects, indicating that the significant correlations have been obtained in both sexes. This means that the correction of the bioelectric impedance can still be carried out by using a parameter derived from the bioelectric impedance value in substitution for the reactance value at the characteristic frequency Fc, Xc, and additionally using an adequate coefficient, and that even such a correction-method allows for an effect equivalent to that could be obtained in the correction using the reactance value as disclosed in the Japanese Patent Application No. 2003-052257. The present invention takes advantage of such a relationship to make a correction on the bioelectric impedance value.

Figure 8:
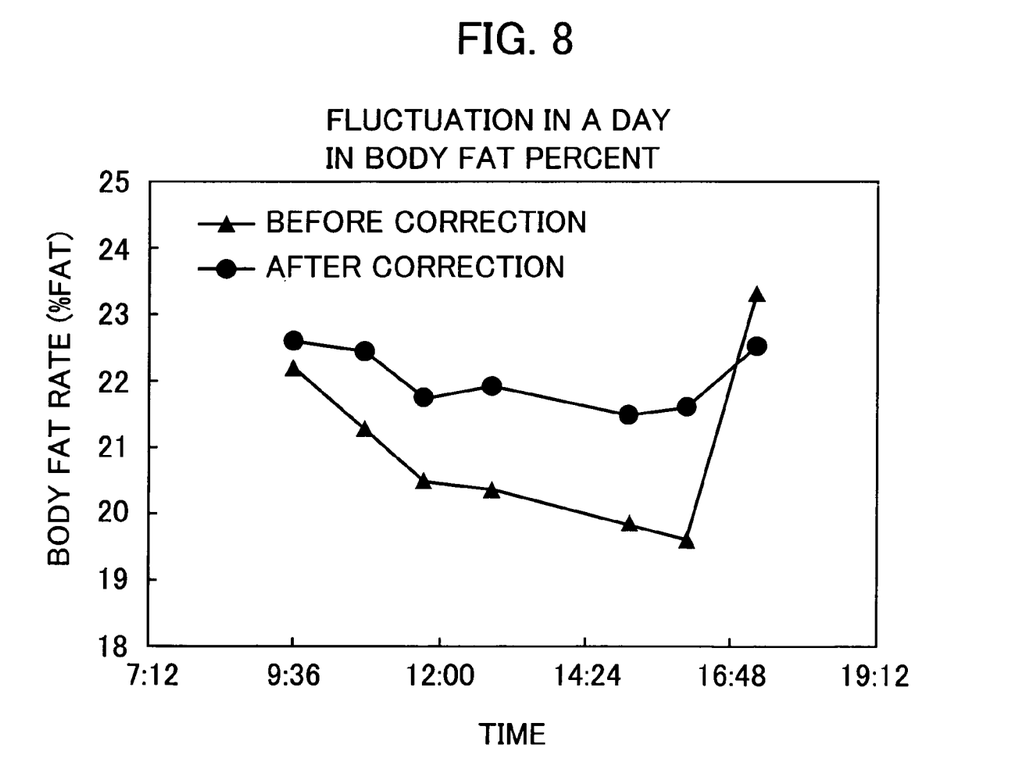
FIG. 8 is a graphical representation indicative of a relationship in calculation of a body fat percentage for a standard person between a case applied with the correction made in accordance with the bioelectric impedance correcting equation of the present invention and a case with no correction applied.

FIG. 8 shows a change in body fat percentage throughout a day for an standard male subject, providing data on the body fat percentage (% FAT) for before to after the application of the equation for the calculation according to the present invention. The equation used for the calculation is:

$$P'=P+[a \times P \times \{Z(F_1)-Z(F_2)\}/Z(F_2)+b],$$

where

P': the corrected index indicative of the body composition,
P: the calculated index indicative of the body composition before correction,
$Z(F_1)$: the bioelectric impedance at the first frequency,
$Z(F_2)$: the bioelectric impedance at the second frequency and
a, b: constants.

Specifically, the body fat percentage (% FAT) was derived from the equation (1) described below by using the bioelectric impedance value at the frequency of 8 kHz, $Z(F_{8k})$, and the bioelectric impedance value at the frequency of 64 kHz, $Z(F_{64k})$.

$$\% \text{ FAT after correction} = \% \text{ FAT before correction} + [-2.96 \times \% \text{ FAT before correction} \times \{Z(F_{8k})-Z(F_{64k})\}/Z(F_{64k})+10.8] \quad (1)$$

It is to be noted that as to the calculation of the body fat percentage (% FAT), since the commercial products have been already available in the market and it has been also disclosed in the reference of the prior art, detailed description should be herein omitted.

Referring to FIG. 8, such tendency can be observed that the value of the body fat percentage gradually decreases from the value in the morning as time goes by and returns back to the high value in the evening for either case of before and after the correction. However, as to the extent of the fluctuation, the fluctuation about 4% has occurred in the body fat percentage before the correction, while the fluctuation has been successfully suppressed to around 1% in the body fat percentage after the correction.

Although only the data on one subject has been here in provided for before and after the correction, the similar results have been obtained for other subjects and the present invention is accordingly considered applicable to the wide range of subjects.

As described above, quite advantageously, it becomes possible to suppress the fluctuation in a day with the effectiveness equivalent to that obtained by the correction method as disclosed in the Japanese Patent Application No. 2003-052257 by applying the present invention to the calculation of the index indicative of the body-composition.

In one specific correction method, the measured bioelectric impedance value may be corrected first and then the index indicative of the body composition may be derived from thus corrected bioelectric impedance value, or the index indicative of the body composition may be corrected after the calculation of the index.

Preferred embodiments of the present invention will now be described with reference to the attached drawings.

Figure 9:
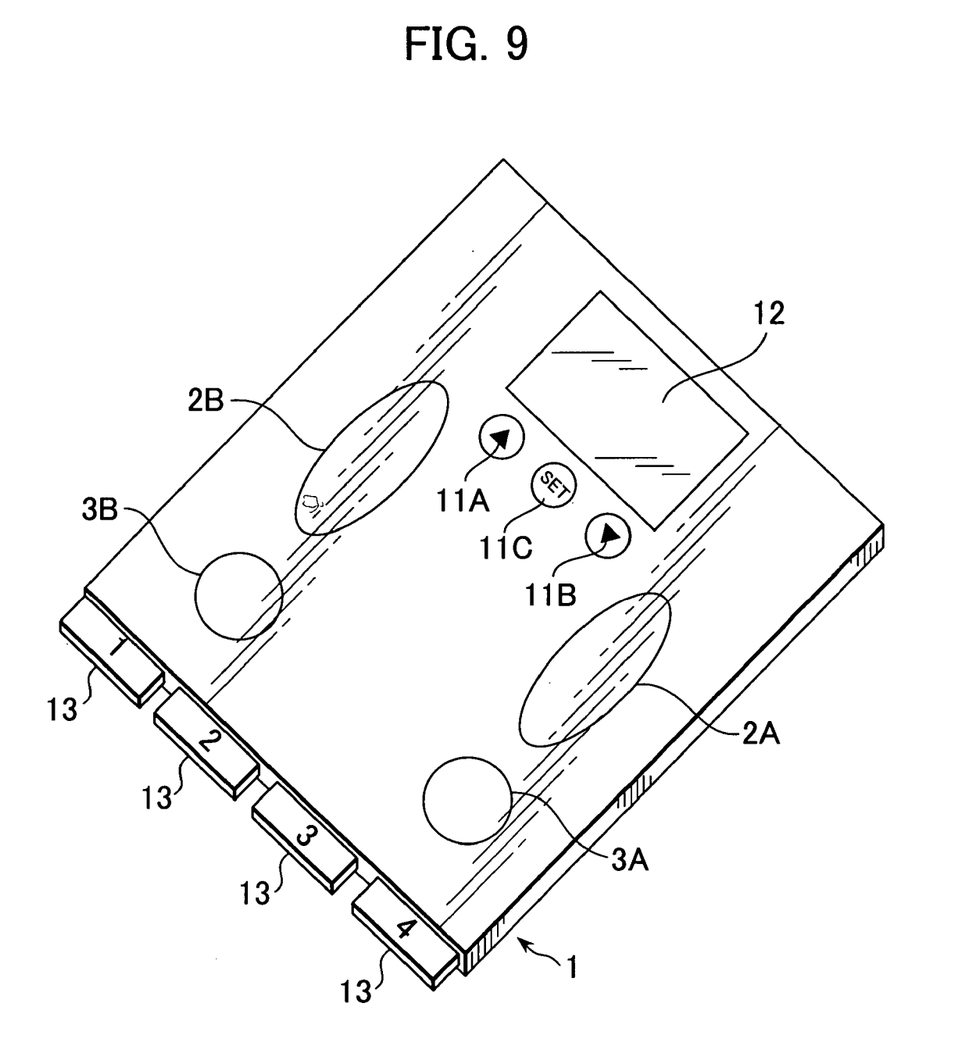
FIG. 9 is an exterior view of a body composition measuring device according to an embodiment of the present invention.
Figure 10:
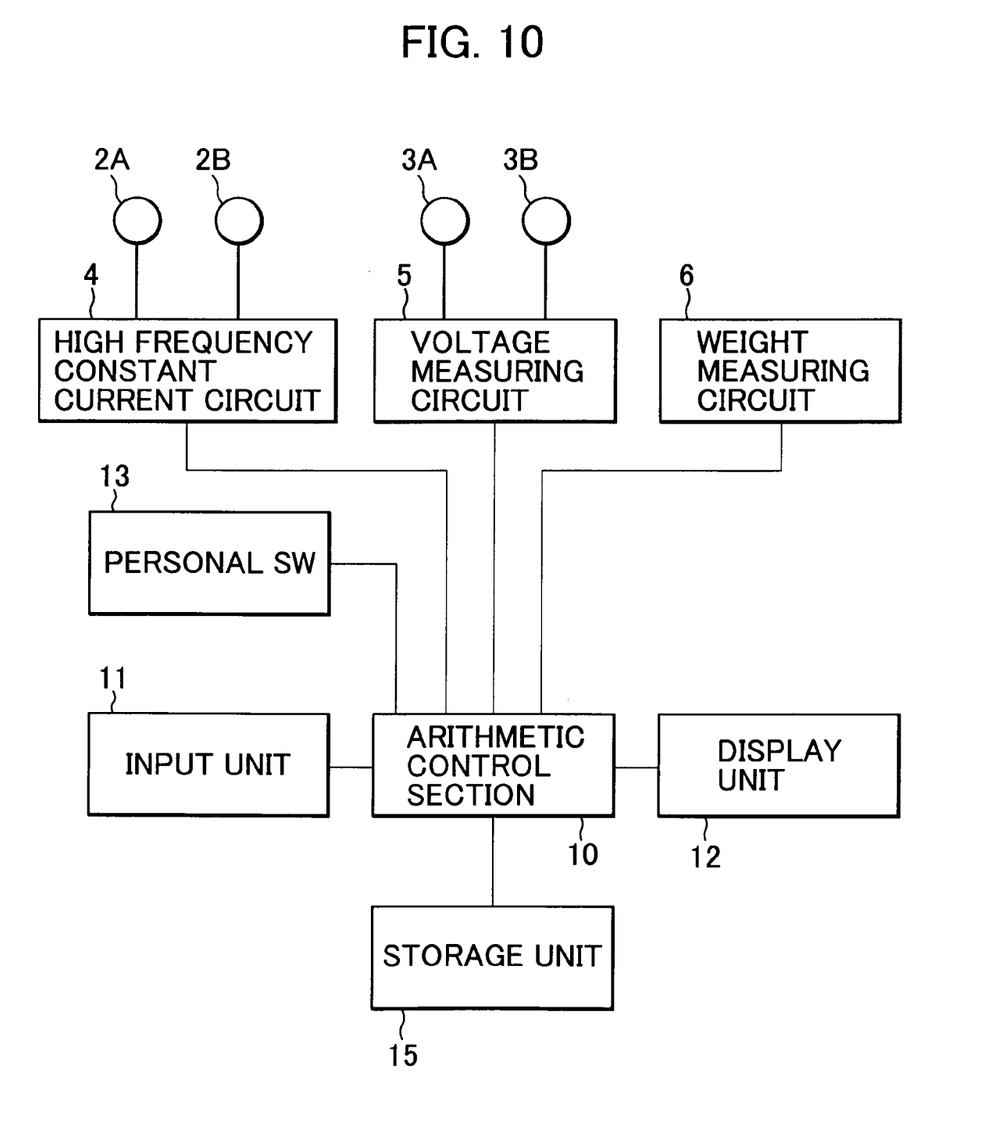
FIG. 10 is an internal block diagram of a body composition measuring device according to an embodiment of the present invention.

FIG. 9 is a perspective exterior view of a body composition measuring device 1 according to the present invention. FIG. 10 is a block diagram showing an internal connection state of the body composition measuring device 1 of FIG. 9.

The body composition measuring device 1 comprises on its top surface four electrodes in total consisting of a pair of current supply electrodes 2A, 2B and a pair of voltage measuring electrodes 3A, 3B, which serve as an impedance measuring means allowing for the impedance between user's feet to be measured.

The pair of current supply electrodes 2A, 2B is connected to a high frequency constant current circuit 4 for applying a high frequency weak constant current to the subject. The other pair of voltage measuring electrodes 3A, 3B is connected to a voltage measuring circuit 5 for measuring a voltage drop due to said constant current. The body composition measuring device 1 includes inside thereof a weight measuring circuit 6 serving as a weight measuring means for measuring a body weight representing the weight of a subject upon loading himself/herself on the body composition measuring device 1. Those voltage measuring circuit 5 and the weight measuring circuit 6 are connected to an arithmetic control section 10 serving as an operating section for executing a conversion from analog value to digital value, a calculation of the body fat percentage and many different control operations.

Further, an input unit 11 serving as an input means for inputting personal data comprises three switches in total consisting of an up switch 11A, a down switch 11B and a setting switch 11C.

The body composition measuring device 1 further comprises a display unit 12 serving as a display means for indicating an entered personal body information and a measured body weight as well as a calculated body fat percentage and the like. The top face of the body composition measuring device 1 further includes a set of personal measuring switches 13.

The body composition measuring device 1 contains in the inside thereof a storage unit 15 serving as a storage means used to store the personal information for a plurality of users and/or to temporarily store the measured body weight value and bioelectric impedance value.

An operation of the body composition measuring device 1 of the present invention will now be described.

Figure 11:
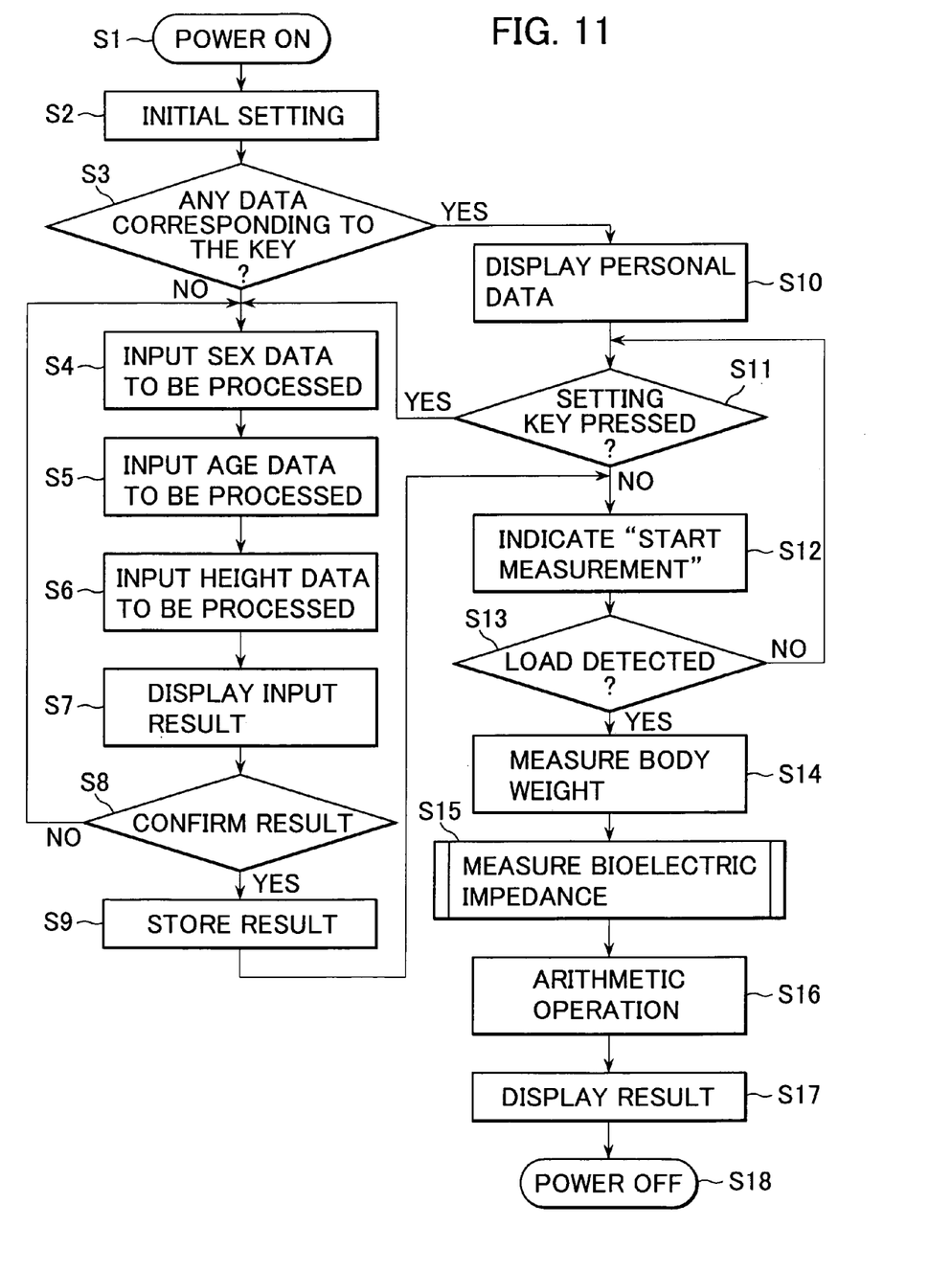
FIG. 11 shows a main flow in a body composition measuring device according to an embodiment of the present invention.

FIG. 11 is a flow chart showing a main flow of the operation in the body composition measuring device 1.

In this body composition measuring device 1, it is required to establish therein a personal body information of a user in advance if it is a first measurement for that user.

When one of the personal measuring switches 13 is pressed, the body composition measuring device 1 is powered on (Step S1), and then initialized to read control program (Step S2). Then, the arithmetic control section 10 decides whether the personal body information has been established in a memory region within the storage unit 13 corresponding to the pressed measuring switch 13 (Step S3).

If the personal body information has not yet been established, the device operates in setting mode. The user uses the up switch 11A and the down switch 11B to alter the information/numeric values indicated in the display unit 12 and then presses the setting switch 11C when a desired set of data is indicated in the display to thereby execute the input operation. By way of this, the user's sex, age and height are successfully input (Steps S4-S6), and each of the entered information is indicated in the display unit 12 (Step S7).

In this stage, if the setting switch 11C is pressed again (Step S8), each of the entered information is stored in the memory region within the storage unit 15 together with the number of one of the measuring switches associated therewith (Step S9).

If Step S3 decides that the personal body information has been already established in the memory region within the storage unit 15 corresponding to the number of the pressed measuring switch 13, the arithmetic control section 10 reads out and then indicates the information in the display unit 12 (Step S10). In this stage, if the setting switch 11C is pressed, then the process moves to the setting mode of the personal information at Step S4 (Step S11).

When the setting of the personal body information has been completed, or if the personal body information has been already established, an indication appears in the display unit 12, in addition to the indication of the personal body information, so as to instruct the user to put his/her body on the top face of the body composition measuring device to start the measurement (Step S12).

Until the load is detected in the weight measuring circuit 6, the device continues the operation of Step S11 for detecting whether or not the setting switch is pressed and the operation of Step S12 for indicating the instruction to the user to put his/her body onto the top face of the body composition measuring device 1 (Step S13).

The user puts his/her body on the body composition measuring device 1 with his/her toe and heel of the right foot touching with the current supply electrode 2A and the voltage measuring electrode 3A, respectively, and with his/her toe and heel of the left foot touching with the current supply electrode 2B and the voltage measuring electrode 3B, respectively. At this timing, the weight measuring circuit 6 measures the body weight of the user (Step S14).

Figure 12:
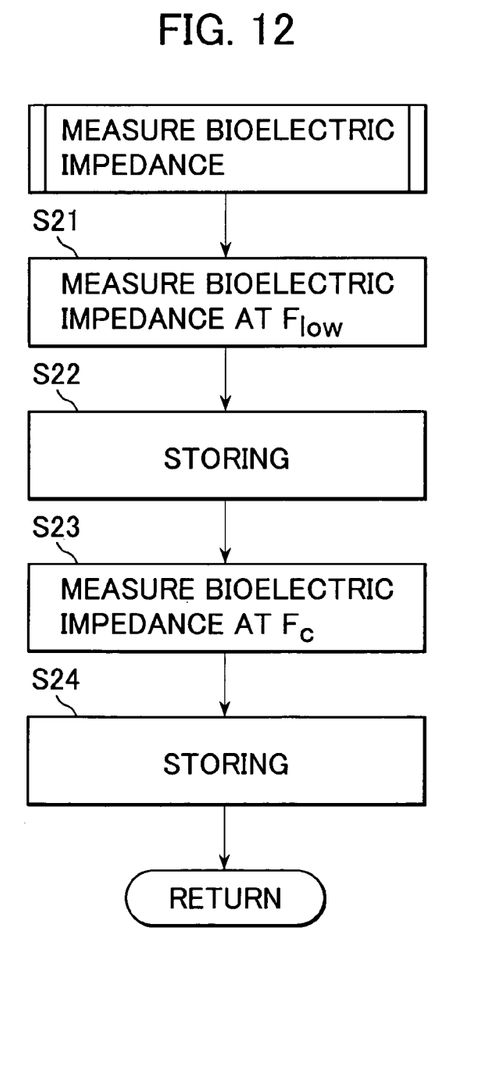
FIG. 12 shows a sub-routine for measuring a bioelectric impedance value in a body composition measuring device according to an embodiment of the present invention.

Subsequently, a bioelectric impedance measurement is executed (Step S15). FIG. 12 shows a sub-routine of the bioelectric impedance measuring procedure.

At first, the measurement of the bioelectric impedance at the measuring frequency of 8 kHz is carried out as a bioelectric impedance measurement at a frequency close to the frequency of 0 Hz. The measuring signal at 8 kHz is generated in the high frequency constant current circuit 4 in accordance with a signal from the arithmetic control section 10 and supplied into the body of the subject via the current supply electrodes 2A, 2B. The voltage between the voltage measuring electrodes 3A and 3B is measured in the voltage measuring circuit 5, while the arithmetic control section 10 calculates the bioelectric impedance value of the subject (Step S21). The calculated bioelectric impedance value is stored in the storage unit 15 (Step S22).

Secondly, the bioelectric impedance measurement at the measuring frequency of 64 kHz is executed as a bioelectric impedance measurement at a frequency close to the characteristic frequency Fc. The measuring signal at 64 kHz is generated in the high frequency constant current circuit 4 in accordance with a signal from the arithmetic control section 10 and supplied into the body of the subject via the current supply electrodes 2A, 2B. The voltage between the voltage measuring electrodes 3A and 3B is measured in the voltage measuring circuit 5, while the arithmetic control section 10 calculates the bioelectric impedance value of the subject (Step S23). The calculated bioelectric impedance value is stored in the storage unit 15 (Step S24).

Figure 13:
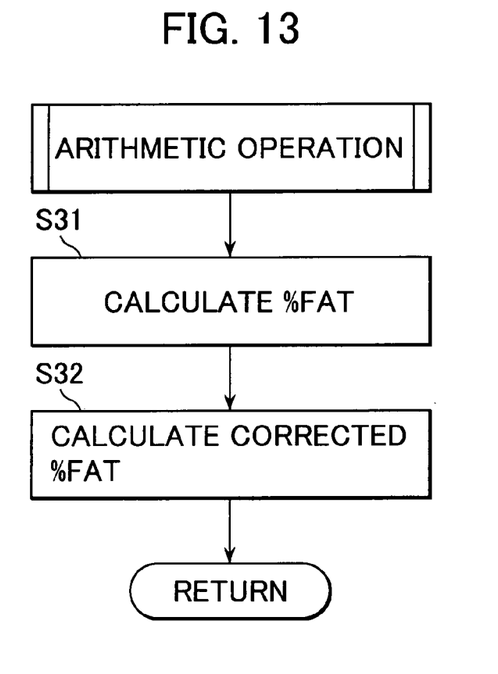
FIG. 13 shows a sub-routine for a computing process of a body fat percentage in a body composition measuring device according to an embodiment of the present invention.

As the measurement of the bioelectric impedance has been completed, the arithmetic operation of the body fat percentage is executed (Step S16). FIG. 13 is a sub-routine of the arithmetic operation.

The arithmetic operation of the body fat percentage is carried out using the measured body weight and the bioelectric impedance value at 64 kHz representing the frequency close to the characteristic frequency together with the stored body information including the height of the user in the storage unit 15 (Step S31). The calculation of the body fat percentage is a known technology, and the detailed description should be herein omitted.

Then, the correcting operation is executed on the calculated body fat percentage. The corrected body fat percentage is calculated by applying the correction in accordance with the above-designated equation (1) using the body fat percentage calculated at Step S31 and the bioelectric impedance values measured at two different frequencies, 8 kHz and 64 kHz, at Step S15 (Step S32).

The calculated corrected body fat percentage is indicated as the measurement result in the display unit 12 (Step S17), and later, after a certain time elapses, the indication in the display unit 12 disappears and the body composition measuring device 1 is powered off (Step S18).

Although the illustrated embodiment of the present invention has taken frequencies of 8 kHz and 64 kHz as the two different measuring frequencies, using those two frequencies is only given by way of example from the reason that they are the frequencies that can be generated easily with a frequency demultiplier of the arithmetic control section, but the frequencies to be used in the measurement are not limited to those.

Further, also as to the measuring frequency zones, although the example using the two different frequencies, the one close to 0 Hz and the other close to the characteristic frequency Fc, has been shown, if such a value that corresponds to the reactance at the characteristic frequency Fc can be obtained, the correction could be made possible with that value. That is, the method may employ two different frequencies designated as the one close to the characteristic frequency Fc and the other close to the infinite frequency, and the difference between the bioelectric impedance values at those frequencies may be applied as the parameter for the correction. Alternatively, the method may employ the frequencies, the one close to 0 Hz and the other close to the infinite frequency, and in this case, one half of the difference between the bioelectric impedance values at those frequencies may be applied as the parameter for the correction.

Further, although in the illustrated embodiment, the body fat percentage is once calculated based on the bioelectric impedance value at a frequency close to the characteristic frequency and later the difference between the bioelectric impedance values at the frequency close to 0 Hz and at the frequency close to the characteristic frequency is applied as the parameter for the correction to thereby calculate the corrected body fat percentage, in an alternative manner, the bioelectric impedance value at the frequency close to the characteristic frequency to be used in the body fat percentage calculation may be directly corrected and then the body fat percentage may be calculated based on the corrected bioelectric impedance value.

Although in the illustrated embodiment, the body fat percentage is illustratively taken as the body composition to be calculated, the present invention is applicable to any component of the body composition that can be calculated based on the measurement of the bioelectric impedance, including the calculation of the indices indicative of the body composition, such as muscle mass, basal metabolic amount, amount of total body water, and bone mass.

What is claimed is:

1. A body composition measuring device comprising: a current applying unit which applies a current at a first frequency and a current at a second frequency to a living body; a voltage measuring unit which measures a voltage induced in the living body from the application of the current; a bioelectric impedance calculation unit which calculates a bioelectric impedance value for each frequency from the applied current and the measured voltage; and a body composition calculation unit which calculates an index indicative of the body composition based on the calculated bioelectric impedance value, said device characterized in that;

said body composition calculation unit corrects the index indicative of the body composition, that has been calculated based on either one of the bioelectric impedance value at the first frequency or the bioelectric impedance value at the second frequency, by using a difference between the bioelectric impedance value at the first frequency and the bioelectric impedance value at the second frequency according to the following equation for correction:

$$P'=P+[a \times P \times \{Z(F_1)-Z(F_2)\}/Z(F_2)+b],$$

where
- $P'$: the corrected index indicative of the body composition;
- $P$: the calculated index indicative of the body composition before correction;
- $Z(F_1)$: the bioelectric impedance at the first frequency;
- $Z(F_2)$: the bioelectric impedance at the second frequency; and
- $a, b$: constants.

* * * * *